(12) United States Patent
Kimura

(10) Patent No.: US 7,622,603 B2
(45) Date of Patent: Nov. 24, 2009

(54) PROCESS FOR PRODUCING δ-AMINOPENTADIENOATE COMPOUND

(75) Inventor: Keizo Kimura, Odawara (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 11/862,372

(22) Filed: Sep. 27, 2007

(65) Prior Publication Data
US 2008/0076940 A1    Mar. 27, 2008

(30) Foreign Application Priority Data
Sep. 27, 2006    (JP)    ............... 2006-263438

(51) Int. Cl.
C07C 255/00    (2006.01)
C07C 317/00    (2006.01)
(52) U.S. Cl. ..................... 558/443; 560/150
(58) Field of Classification Search ............... None
See application file for complete search history.

(56) References Cited

U.S. PATENT DOCUMENTS

| | | |
|---|---|---|
| 2,165,339 A | 7/1939 | Brooker |
| 2,186,608 A | 1/1940 | Keyes et al. |
| 7,323,589 B2 * | 1/2008 | Valla et al. .................. 560/171 |

FOREIGN PATENT DOCUMENTS

JP    2003277349 A    10/2003

OTHER PUBLICATIONS

Frances M. Hamer, "The Cyanine Dyes and Related Compounds", Formerly Research Chemist, Kodak Ltd., London, and Honorary Lecturer, Imperial College of Science and Technology, London, 1964, pp. 488-495, Interscience Publishers.

Vasu Nair et al., "Selective Alkylation Reactions With Vinamidinium Salts", Department of Chemistry, University of Iowa, Iowa City, Iowa 52242, Apr. 23, 1980, Tetrahedron Letters, pp. 3155-3158, vol. 21.

* cited by examiner

*Primary Examiner*—Paul A Zucker
(74) *Attorney, Agent, or Firm*—Sughrue Mion, PLLC

(57) ABSTRACT

Disclosed is a process for producing a δ-aminopentadienoate compound represented by the following formula (I), the process including reacting a δ-aminopentadienoate compound represented by the following formula (II) with an alcohol represented by the following formula (III):

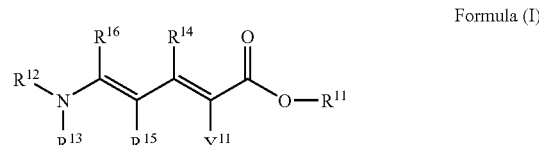

Formula (I)

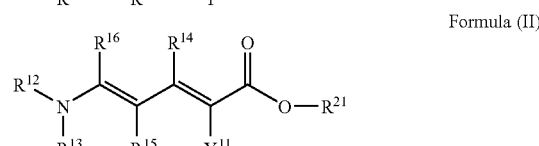

Formula (II)

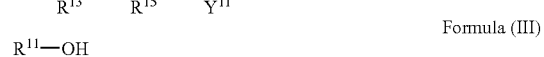

Formula (III)

wherein in formulae (I to III) $R^{11}$ and $R^{21}$ each independently represent an aliphatic group, an aromatic group, or a heterocyclic group bonded via a carbon atom; $R^{12}$ to $R^{16}$ each independently represent a hydrogen atom, an aliphatic group, an aromatic group, or a heterocyclic group bonded via a carbon atom; $Y^{11}$ represents an electron-withdrawing group; and $R^{11}$ and $R^{21}$ are not the same group.

16 Claims, No Drawings

PROCESS FOR PRODUCING δ-AMINOPENTADIENOATE COMPOUND

CROSS-REFERENCE TO RELATED APPLICATION

This Application claims priority under 35 USC 119 from Japanese Patent Application No. 2006-263438, the disclosure of which is incorporated by reference herein.

BACKGROUND OF THE INVENTION

1. Field of the Invention

The present invention relates to a process for producing a δ-aminopentadienoate compound (which may also be referred to as a δ-aminopentadienoate derivative).

2. Description of the Related Art

Processes for producing a δ-aminopentadienoate derivative have been known for a long time; for example, a process producing a δ-aminopentadienoate derivative via a dianil derivative has been disclosed (see, for example, U.S. Pat. Nos. 2,165,339, 2,186,608, and F. M. Hamer: The Cyanine Dyes and Related Compounds—The Chemistry of Heterocyclic Compounds Vol. 18, John Wiley & Sons, New York, London, 1964, Chapter XIII, p. 488-494). However, the reaction pathway of these processes is long, and the total yield is low.

A process has also been disclosed for producing a δ-aminopentadienoate derivative by reacting a streptocyanine derivative with a carbonyl compound in the presence of sodium hydride and triethylamine (see, for example, Tetrahedron Letters, vol. 21, p. 3,155 (1980)), but the sodium hydride used in this process is flammable and thus not suited for industrial purposes; furthermore, the yield is low.

As a production process overcoming these problems, a process that involves reacting a streptocyanine derivative with a carbonyl compound in the presence of a safe organic base has been disclosed (see, for example, Japanese Patent Application Laid-Open (JP-A) No. 2003-277349). In this process, however, an acetate derivative is used, and when the number of carbon atoms in an alkyl group of the ester is large (the number of carbons is 8 or more), the reactivity is lowered, resulting in a lower yield, and thus there is a demand for a process for production giving a high yield even with an alkyl group having a high number of carbon atoms.

SUMMARY OF THE INVENTION

According to an aspect of the present invention, there is provided a process for producing a δ-aminopentadienoate derivative represented by the following formula (I), the process including reacting a δ-aminopentadienoate compound represented by the following formula (II) with an alcohol represented by the following formula (III):

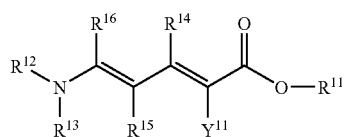

Formula (I)

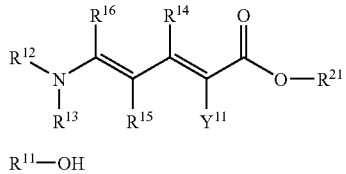

Formula (II)

$R^{11}$—OH

Formula (III)

wherein in formulae (I) to (III), $R^{11}$ and $R^{21}$ each independently represent an aliphatic group, an aromatic group, or a heterocyclic group bonded via a carbon atom; $R^{12}$, $R^{13}$, $R^{14}$, $R^{15}$ and $R^{16}$ each independently represent a hydrogen atom, an aliphatic group, an aromatic group, or a heterocyclic group bonded via a carbon atom; $Y^{11}$ represents an electron-withdrawing group; $R^{12}$ and $R^{13}$ may be bonded to each other to form a ring; $R^{13}$ and $R^{15}$ may be bonded to each other to form a ring; $R^{15}$ and $Y^{11}$ may be bonded to each other to form a ring; $Y^{11}$ and $R^{11}$ may be bonded to each other to form a ring; $Y^{11}$ and $R^{21}$ may be bonded to each other to form a ring; $R^{11}$ and $R^{14}$ may be bonded to each other to form a ring; $R^{21}$ and $R^{14}$ may be bonded to each other to form a ring; $R^{14}$ and $R^{16}$ may be bonded to each other to form a ring; $R^{16}$ and $R^{12}$ may be bonded to each other to form a ring; and $R^{11}$ and $R^{21}$ are not the same group.

DETAILED DESCRIPTION OF THE INVENTION

The process for producing a δ-aminopentadienoate derivative according to an aspect of the present invention (hereinafter referred to sometimes as the "production process of an aspect of the invention") includes reacting a δ-aminopentadienoate derivative represented by formula (II) below with an alcohol represented by formula (III) below. According to the production process of an aspect of the invention, a δ-aminopentadienoate derivative having a group bonded to a desired carboxylic acid, represented by formula (I) below, can be produced safely and economically with a high yield.

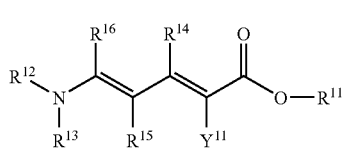

Formula (I)

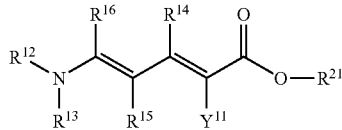

Formula (II)

$R^{11}$—OH

Formula (III)

In formulae (I) to (III), $R^{11}$ and $R^{21}$ each independently represent an aliphatic group, an aromatic group, or a heterocyclic group bonded via a carbon atom; $R^{12}$, $R^{13}$, $R^{14}$, $R^{15}$ and $R^{16}$ each independently represent a hydrogen atom, an aliphatic group, an aromatic group, or a heterocyclic group bonded via a carbon atom; $Y^{11}$ represents an electron-withdrawing group; $R^{12}$ and $R^{13}$ may be bonded to each other to form a ring; $R^{13}$ and $R^{15}$ may be bonded to each other to form a ring; $R^{15}$ and $Y^{11}$ may be bonded to each other to form a ring; $Y^{11}$ and $R^{11}$ may be bonded to each other to form a ring; $Y^{11}$ and $R^{21}$ may be bonded to each other to form a ring; $R^{11}$ and $R^{14}$ may be bonded to each other to form a ring; $R^{21}$ and $R^{14}$ may be bonded to each other to form a ring; $R^{14}$ and $R^{16}$ may be bonded to each other to form a ring; $R^{16}$ and $R^{12}$ may be bonded to each other to form a ring; and $R^{11}$ and $R^{21}$ are not the same group.

Hereinafter, embodiments of the invention are described in more detail.

(Groups in the Invention)

Before the compounds in the production process of an aspect of the invention are described, the groups in the invention will be described in detail.

Preferable examples of the aliphatic group in the present specification include an alkyl group, a substituted alkyl group, an alkenyl group, a substituted alkenyl group, an alkynyl group, a substituted alkynyl group, an aralkyl group and a substituted aralkyl group.

The alkyl group may be branched or may form a ring. The number of carbon atoms in the alkyl group is preferably 1 to 20, more preferably 1 to 18. The alkyl moiety of the substituted alkyl group is the same as the above alkyl group.

The alkenyl group may be branched or may form a ring. The number of carbon atoms in the alkenyl group is preferably 2 to 20, more preferably 2 to 18.

The alkenyl moiety of the substituted alkenyl group is similar to the above alkenyl group.

The alkynyl group may be branched or may form a ring. The number of carbon atoms in the alkynyl group is preferably 2 to 20, more preferably 2 to 18.

The alkynyl moiety of the substituted alkynyl group is similar to the above alkynyl group.

The alkyl moiety of the aralkyl group and substituted aralkyl group is similar to the above alkyl group. The aryl moiety of the aralkyl group and substituted aralkyl group is similar to the aryl group described later.

Examples of substituent groups in the substituted alkyl group, in the substituted alkenyl group, in the substituted alkynyl group and in the alkyl moiety of the substituted aralkyl group include halogen atoms (for example, a chlorine atom, bromine atom, and iodine atom), alkyl groups [straight-chain, branched, or cyclic substituted or unsubstituted alkyl group; specific examples thereof include alkyl groups (preferably alkyl groups having 1 to 30 carbon atoms, such as methyl, ethyl, n-propyl, isopropyl, t-butyl, n-octyl, eicosyl, 2-chloroethyl, 2-cyanoethyl, and 2-ethylhexyl), cycloalkyl groups (preferably, substituted or unsubstituted cycloalkyl groups having 3 to 30 carbon atoms, such as cyclohexyl, cyclopentyl, and 4-n-dodecylcyclohexyl), bicycloalkyl groups (preferably, substituted or unsubstituted bicycloalkyl groups having 5 to 30 carbon atoms, that is, monovalent groups of bicycloalkane having 5 to 30 carbon atoms from which one hydrogen atom was removed, such as bicyclo[1,2,2]heptan-2-yl and bicyclo[2,2,2]octan-3-yl), tricycle structures containing more cyclic structures, and the like; and an alkyl group in a substituent group described below (for example, an alkyl group in an alkylthio group) is also the alkyl group in the same meaning], alkenyl groups [straight-chain, branched or cyclic substituted or unsubstituted alkenyl groups; alkenyl groups (including preferably, substituted or unsubstituted alkenyl groups having 2 to 30 carbon atoms, such as vinyl, allyl, prenyl, geranyl, and oleyl), including cycloalkenyl groups (preferably, substituted or unsubstituted cycloalkenyl groups having 3 to 30 carbon atoms, that is, monovalent groups of cycloalkene having 3 to 30 carbon atoms, from which one hydrogen atom was removed, such as 2-cyclopenten-1-yl and 2-cyclohexen-1-yl), and bicycloalkenyl groups (substituted or unsubstituted bicycloalkenyl groups, preferably substituted or unsubstituted bicycloalkenyl groups having 5 to 30 carbon atoms, that is, monovalent groups of bicycloalkene having one double bond from which one hydrogen atom was removed, for example, bicyclo[2,2,1]hept-2-en-1-yl and bicyclo[2,2,2]oct-2-en-4-yl)], alkynyl groups (preferably, substituted or unsubstituted alkynyl groups having 2 to 30 carbon atoms, such as ethynyl, propargyl, and trimethylsilylethynyl), aryl groups (preferably, substituted or unsubstituted aryl groups having 6 to 30 carbon atoms, such as phenyl, p-tolyl, naphthyl, m-chlorophenyl, and o-hexadecanoylaminophenyl), heterocyclic groups (monovalent groups, preferably five- or six-membered substituted or unsubstituted, aromatic or non-aromatic heterocyclic compounds from which one hydrogen atom was removed, more preferably, five- or six-membered heteroaromatic ring groups having 3 to 30 carbon atoms, such as 1-pyrazolyl, 2-furyl, 2-thienyl, 2-pyrimidinyl, and 2-benzothiazolyl), a cyano group, a hydroxyl group, a nitro group, a carboxyl group, alkoxy groups (preferably, substituted or unsubstituted alkoxy groups having 1 to 30 carbon atoms, such as methoxy, ethoxy, isopropoxy, t-butoxy, n-octyloxy, and 2-methoxyethoxy), aryloxy groups (preferably, substituted or unsubstituted aryloxy groups having 6 to 30 carbon atoms, such as phenoxy, 2-methylphenoxy, 4-t-butylphenoxy, 3-nitrophenoxy, and 2-tetradecanoylaminophenoxy), silyloxy groups (preferably silyloxy groups having 3 to 20 carbon atoms, such as trimethylsilyloxy and t-butyldimethylsilyloxy), heterocyclic oxy groups (preferably, substituted or unsubstituted heterocyclic oxy groups having 2 to 30 carbon atoms, such as 1-phenyltetrazol-5-oxy and 2-tetrahydropyranyloxy), acyloxy groups (preferably, a formyloxy group, substituted or unsubstituted alkylcarbonyloxy groups having 2 to 30 carbon atoms, and substituted or unsubstituted arylcarbonyloxy groups having 6 to 30 carbon atoms, such as formyloxy, acetyloxy, pivaloyloxy, stearoyloxy, benzoyloxy, and p-methoxyphenylcarbonyloxy), carbamoyloxy groups (preferably, substituted or unsubstituted carbamoyloxy group having 1 to 30 carbon atoms, such as N,N-dimethylcarbamoyloxy, N,N-diethylcarbamoyloxy, morpholinocarbonyloxy, N,N-di-n-octylaminocarbonyloxyl, and N-n-octylcarbamoyloxy), alkoxycarbonyloxy groups (preferably, substituted or unsubstituted alkoxycarbonyloxy groups having 2 to 30 carbon atoms, such as methoxycarbonyloxy, ethoxycarbonyloxy, t-butoxycarbonyloxy, and n-octylcarbonyloxy), aryloxycarbonyloxy groups (preferably, substituted or unsubstituted aryloxycarbonyloxy groups having 7 to 30 carbon atoms, such as phenoxycarbonyloxy, p-methoxyphenoxycarbonyloxy, and p-n-hexadecyloxyphenoxycarbonyloxy), amino groups (preferably, an amino group, substituted or unsubstituted alkylamino groups having 1 to 30 carbon atoms, and substituted or unsubstituted anilino groups having 6 to 30 carbon atoms, such as amino, methylamino, dimethylamine, anilino, N-methyl-anilino, and diphenylamino), acylamino groups (preferably, a formylamino group, substituted or unsubstituted alkylcarbonylamino groups having 1 to 30 carbon atoms, and substituted or unsubstituted arylcarbonylamino groups having 6 to 30 carbon atoms, such as formylamino, acetylamino, pivaloylamino, lauroylamino, benzoylamino, and 3,4,5-tri-n-octyloxyphenylcarbonylamino), aminocarbonylamino groups (preferably, substituted or unsubstituted aminocarbonylamino groups having 1 to 30 carbon atoms, such as carbamoylamino, N,N-dimethylaminocarbonylamino, N,N-diethylaminocarbonylamino, and morpholinocarbonylamino), alkoxycarbonylamino groups (preferably, substituted or unsubstituted alkoxycarbonylamino groups having 2 to 30 carbon atoms, such as methoxycarbonylamino, ethoxycarbonylamino, t-butoxycarbonylamino, n-octadecyloxycarbonylamino, and N-methylmethoxycarbonylamino), aryloxycarbonylamino groups (preferably, substituted or unsubstituted aryloxycarbonylamino groups having 7 to 30 carbon atoms, such as phenoxycarbonylamino, p-chlorophenoxycarbonylamino, and m-n-octyloxyphenoxycarbonylamino), sulfamoylamino groups (preferably, substituted or unsubstituted sulfamoylamino groups having 0 to 30 carbon atoms, such as sulfamoylamino, N,N-dimethylaminosulfonylamino, and N-n-octylaminosulfonylamino), alkyl and arylsulfonylamino groups (preferably, substituted or unsubstituted alkylsulfonylamino groups having 1 to 30 carbon atoms, and substituted or unsubstituted arylsulfonylamino groups having 6 to 30 carbon atoms, such as methylsulfonylamino, butylsulfonylamino, phenylsulfonylamino, 2,3,5-trichlorophenylsulfonylamino, and p-methylphenylsulfonylamino), a mercapto group, alkylthio groups (preferably, substituted or unsubstituted alkylthio groups having 1 to 30 carbon atoms, such as methylthio, ethylthio, and n-hexadecylthio), arylthio groups (preferably, substituted or unsubstituted arylthio groups having 6 to 30 carbon atoms, such as phenylthio, p-chlorophenylthio, and m-methoxyphenylthio), heterocyclic thio groups (preferably, substituted or unsubstituted heterocyclic thio groups having 2 to 30 carbon atoms, such as 2-benzothiazolylthio and 1-phenyltetrazol-5-yl-thio), sulfamoyl groups (preferably, substituted or unsubstituted sulfamoyl groups having 0 to 30 carbon atoms, such as N-ethylsulfamoyl, N-(3-dodecyloxypropyl)sulfamoyl, N,N-dimethylsulfamoyl, N-acetylsulfamoyl, N-benzoylsulfamoyl, and N-(N')-phenylcarbamoyl)sulfamoyl), a sulfo group, alkyl or arylsulfinyl groups (preferably, substituted or unsubstituted alkylsulfinyl groups having 1 to 30 carbon atoms and substituted or unsubstituted arylsulfinyl groups having 6 to 30 carbon atoms, such as methylsulfinyl, ethylsulfinyl, phenylsulfinyl, and p-methylphenylsulfinyl), alkyl or arylsulfonyl groups (preferably, substituted or unsubstituted alkylsulfonyl groups having 1 to 30 carbon atoms and substituted or unsubstituted arylsulfonyl groups having 6 to 30 carbon atoms, such as methylsulfonyl, ethylsulfonyl, phenylsulfonyl, and p-methylphenylsulfonyl), acyl groups (preferably a formyl group, substituted or unsubstituted alkylcarbonyl groups having 2 to 30 carbon atoms, substituted or unsubstituted arylcarbonyl groups having 7 to 30 carbon atoms, and substituted or unsubstituted heterocyclic carbonyl groups having 4 to 30 carbon atoms in which a carbonyl group is bonded to a carbon atom, such as acetyl, pivaloyl, 2-chloroacetyl, stearoyl, benzoyl, p-n-octyloxyphenylcarbonyl, 2-pyridylcarbonyl, and 2-furylcarbonyl), aryloxycarbonyl groups (preferably, substituted or unsubstituted aryloxycarbonyl groups having 7 to 30 carbon atoms, such as phenoxycarbonyl, o-chlorophenoxycarbonyl, m-nitrophenoxycarbonyl, and p-t-butylphenoxycarbonyl), alkoxycarbonyl groups (preferably, substituted or unsubstituted alkoxycarbonyl groups having 2 to 30 carbon atoms, such as methoxycarbonyl, ethoxycarbonyl, t-butoxycarbonyl, and n-octadecyloxycarbonyl), carbamoyl groups (preferably, substituted or unsubstituted carbamoyl groups having 1 to 30 carbon atoms, such as carbamoyl, N-methylcarbamoyl, N,N-dimethylcarbamoyl, N,N-di-n-octylcarbamoyl, and N-(methylsulfonyl)carbamoyl), aryl or heterocyclic azo groups (preferably, substituted or unsubstituted arylazo groups having 6 to 30 carbon atoms and substituted or unsubstituted heterocyclic azo groups having 3 to 30 carbon atoms, such as phenylazo, p-chlorophenylazo, and 5-ethylthio-1,3,4-thiadiazol-2-ylazo), imido groups (preferably, N-succinimido and N-phthalimido), phosphino groups (preferably, substituted or unsubstituted phosphino groups having 2 to 30 carbon atoms, such as dimethylphosphino, diphenylphosphino, and methylphenoxyphosphino), phosphinyl groups (preferably, substituted or unsubstituted phosphinyl groups having 2 to 30 carbon atoms, such as phosphinyl, dioctyloxyphosphinyl, and diethoxyphosphinyl), phosphinyloxy groups (preferably, substituted or unsubstituted phosphinyloxy groups having 2 to 30 carbon atoms, such as diphenoxyphosphinyloxy and dioctyloxyphosphinyloxy), phosphinylamino groups (preferably, substituted or unsubstituted phosphinylamino groups having 2 to 30 carbon atoms, such as dimethoxyphosphinylamino and dimethylaminophosphinylamino), silyl groups (preferably, substituted or unsubstituted silyl groups having 3 to 30 carbon atoms, such as trimethylsilyl, t-butyldimethylsilyl, and phenyldimethylsilyl), and the like.

Among the functional groups above, those containing a hydrogen atom may be deprived of their hydrogen atom and substituted by one of the above groups in place of the hydrogen atom. Examples of such functional groups include alkylcarbonylaminosulfonyl groups, arylcarbonylaminosulfonyl groups, alkylsulfonylaminocarbonyl groups, and arylsulfonylaminocarbonyl groups. Specific examples include a methylsulfonylaminocarbonyl group, a p-methylphenylsulfonylaminocarbonyl group, an acetylaminosulfonyl group, and a benzoylaminosulfonyl group.

Substituent groups in the aryl moiety of the substituted aralkyl group include the substituent groups in the following substituted aryl group.

The aromatic group in the present specification means an aryl group or a substituted aryl group. These aromatic groups may be fused with an aliphatic ring, another aromatic ring or hetero ring. The number of carbon atoms in the aromatic group is preferably 6 to 40, more preferably 6 to 30, and still more preferably 6 to 20. Among them, the aryl group is preferably a phenyl or naphthyl group, particularly preferably a phenyl group.

The aryl moiety of the substituted aryl group is similar to the aryl group described above. Examples of substituent groups in the substituted aryl group include those mentioned in the examples of substituent groups in the substituted alkyl group, in the substituted alkenyl group, in the substituted alkynyl group and in the alkyl moiety of the substituted aralkyl group.

In the present specification, the heterocyclic group preferably contains a 5- or 6-membered saturated or unsaturated heterocycle. An aliphatic ring, an aromatic ring or another heterocycle may be fused with the heterocycle. Examples of a heteroatom in the heterocycle include B, N, O, S, Se and Te. The heteroatom is preferably N, O or S. Preferably, a carbon atom in the heterocycle has a free atomic valence (monovalent) (heterocyclic group is bonded via the carbon atom).

The number of carbon atoms in the heterocyclic group is preferably 1 to 40, more preferably 1 to 30, still more preferably 1 to 20. Examples of the saturated heterocycle include a pyrrolidine ring, morpholine ring, 2-bora-1,3-dioxolane ring, and 1,3-thiazolidine ring. Examples of the unsaturated heterocycle include an imidazole ring, thiazole ring, benzothiazole ring, benzoxazole ring, benzotriazole ring, benzoselenazole ring, pyridine ring, pyrimidine ring and quinoline ring. The heterocyclic group may have a substituent group. Examples of such substituent groups include those mentioned in the examples of substituent groups in the substituted alkyl group, in the substituted alkenyl group, in the substituted alkynyl group and in the alkyl moiety of the substituted aralkyl group.

Now, the compounds represented by formulae (I) to (III) are described. From the viewpoint of excellent reaction yield, $R^{11}$ in formulae (I) and (III) is preferably an aliphatic group or an aromatic group, more preferably an alkyl group having 4 to 30 carbon atoms, an alkenyl group having 4 to 30 carbon atoms, an alkynyl group having 4 to 30 carbon atoms, an aralkyl group having 7 to 30 carbon atoms or an aryl group having 6 to 30 carbon atoms, still more preferably an alkyl group having 6 to 20 carbon atoms, an alkenyl group having 6 to 20 carbon atoms, an aralkyl group having 7 to 20 carbon atoms, or an aryl group having 6 to 20 carbon atoms, further more preferably an alkyl group having 6 to 20 carbon atoms or an alkenyl group having 6 to 20 carbon atoms, most preferably a primary alkyl group having 8 to 20 carbon atoms.

Each of $R^{12}$ and $R^{13}$ in formulae (I) and (II) is preferably a hydrogen atom, an alkyl group, an alkenyl group, an alkynyl group or an aryl group, more preferably a hydrogen atom, an alkyl group having 1 to 20 carbon atoms, an alkenyl group having 2 to 20 carbon atoms, an alkynyl group having 2 to 20 carbon atoms, or an aryl group having 6 to 20 carbon atoms, still more preferably an alkyl group having 1 to 10 carbon atoms, an alkenyl group having 2 to 10 carbon atoms, or an aryl group having 6 to 10 carbon atoms, further more preferably an alkyl group having 1 to 8 carbon atoms or an aryl group having 6 to 8 carbon atoms, most preferably a primary alkyl group having 1 to 5 carbon atoms. It is also preferable that $R^{12}$ and $R^{13}$ are the same.

Each of $R^{14}$, $R^{15}$ and $R^{16}$ in formulae (I) and (II) is preferably a hydrogen atom, an alkyl group having 1 to 10 carbon atoms, or an aryl group having 6 to 10 carbon atoms, more preferably a hydrogen atom or an alkyl group having 1 to 5 carbon atoms, still more preferably a hydrogen atom.

Because the raw material is easily available and alcohol as a byproduct in the reaction of the invention is easily distilled away, $R^{21}$ in formula (II) is preferably an aliphatic group or an aromatic group, more preferably an alkyl group having 1 to 5 carbon atoms, an alkenyl group having 2 to 5 carbon atoms, or an alkynyl group having 2 to 5 carbon atoms, still more preferably an alkyl group having 1 to 4 carbon atoms or an alkenyl group having 2 to 4 carbon atoms, further more preferably an alkyl group having 1 to 4 carbon atoms, even more preferably a methyl group or an ethyl group, most preferably an ethyl group.

Preferably, $R^{11}$ and $R^{21}$ are not the same, and the number of carbon atoms in $R^{11}$ is greater by at least 4 than $R^{21}$.

The electron-withdrawing groups represented by $Y^{11}$ in formulae (I) and (II) represent a substituent group whose Hammett's substituent constant $\sigma_p$ value is a positive numerical value. The Hammett's rule is an empirical rule proposed by L. P. Hammett in 1935 to quantitatively discuss the influence of substituent groups on the reaction or equilibrium of benzene derivatives, and nowadays the validity of this rule is widely recognized. The substituent constant determined by the Hammett's rule includes $\sigma_p$ value and $\sigma_m$ value, and these values can be found in many books, and are detailed in, for example, J. A. Dean: Lange's Handbook of Chemistry, 12th ed. (1979), McGraw-Hill, and "Kagaku No Ryoiki (Area of Chemistry), Special Number", No. 122, pp. 96 to 103 (1979), (Nankodo, J P). In the invention, $Y^{11}$ may be defined by the Hammett's substituent constant $\sigma_p$ value, but this does not mean that the substituent groups are limited to those having known values found in the above books, but means that the substituent groups also include those having Hammett's constant $\sigma_p$ values which when measured according to the Hammett's rule, are in the range defined in the invention even if their values are not known.

Preferable examples of $Y^{11}$ in formulae (I) and (II) above include an alkylsulfonyl group, an arylsulfonyl group, an acyl group, an arylcarbonyl group, a cyano group, an alkoxycarbonyl group, or an aryloxycarbonyl group.

The group represented by $Y^{11}$ will be described in more detail. $Y^{11}$ may be an arylsulfonyl group having preferably 6 to 20 carbon atoms, more preferably 6 to 15 carbon atoms (for example, a benzenesulfonyl group, a p-toluenesulfonyl group, a p-chlorobenzenesulfonyl group and a naphthalenesulfonyl group), an acyl group having preferably 1 to 20 carbon atoms, more preferably 1 to 5 carbon atoms (for example, a formyl group, an acetyl group and a propionyl group), an arylcarbonyl group having preferably 7 to 20 carbon atoms, more preferably 7 to 15 carbon atoms, a nitrile group, an alkoxycarbonyl group having preferably 2 to 20 carbon atoms, more preferably 2 to 9 carbon atoms (for example, a methoxycarbonyl group, an ethoxycarbonyl group, a t-butoxycarbonyl group and a benzyloxycarbonyl group), and an aryloxycarbonyl group having preferably 7 to 20 carbon atoms, more preferably 7 to 15 carbon atoms (for example, a phenoxycarbonyl group and a p-nitrophenoxycarbonyl group). Among these, an arenesulfonyl group having 6 to 15 carbon atoms is preferable, and a benzenesulfonyl group is more preferable.

Hereinafter, exemplary compounds (I-1) to (I-20) are shown as specific examples of the compounds represented by formula (I); exemplary compounds (II-1) to (II-10) are shown as specific examples of the compounds represented by formula (II); and exemplary compounds (III-1) to (III-10) are shown as specific examples of the compounds represented by formula (III). However, the invention is not limited thereto. In the following specific examples, "Ph" represents a phenyl group.

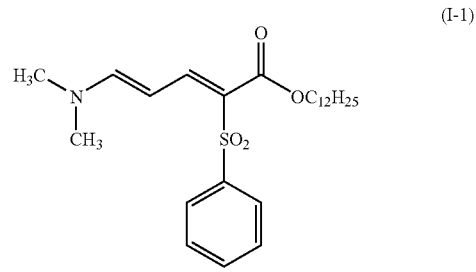

(I-1)

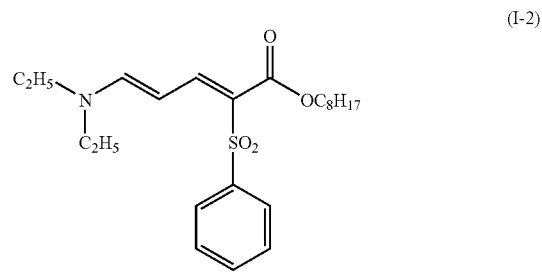

(I-2)

-continued
(I-3)
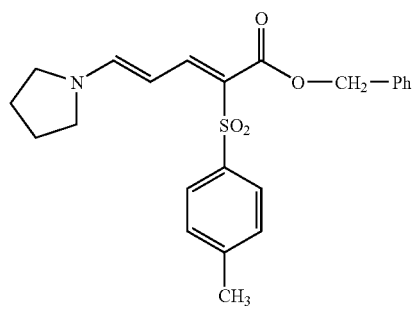
(I-4)
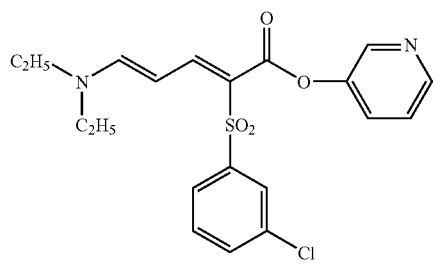
(I-5)
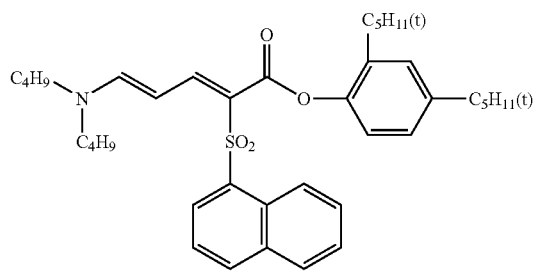
(I-6)
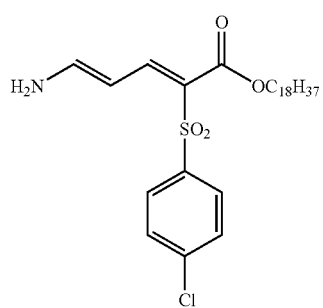
(I-7)
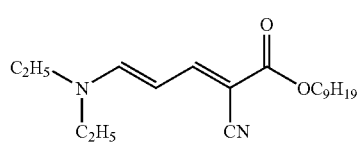
(I-8)
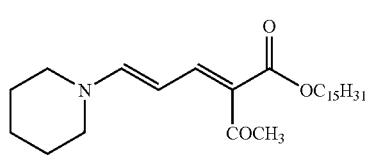
-continued
(I-9)
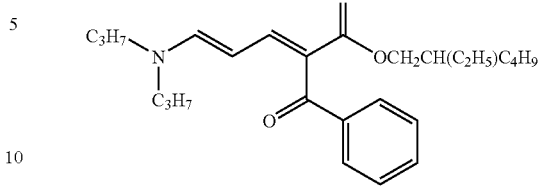
(I-10)
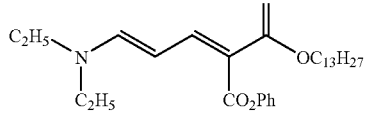
(I-11)
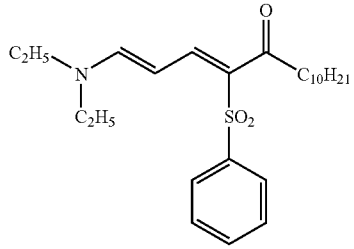
(I-12)
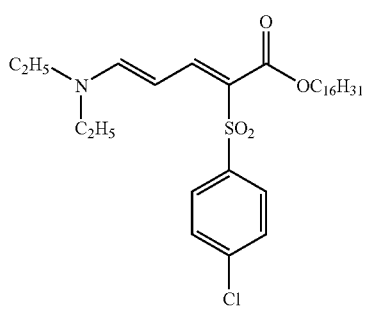
(I-13)
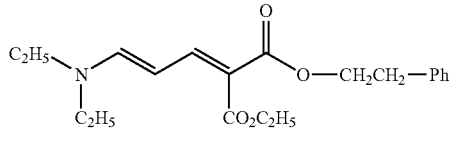
(I-14)
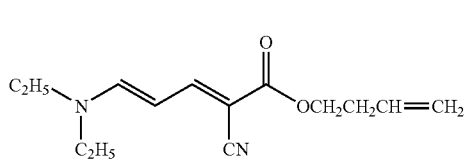
(I-15)
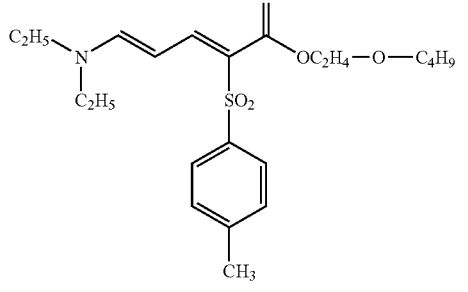

(I-16)
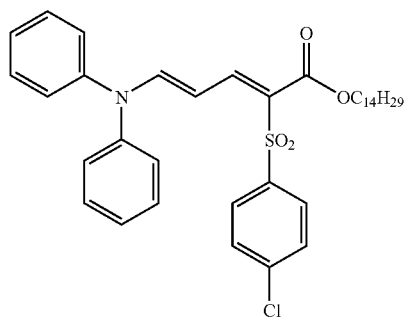
(I-17)
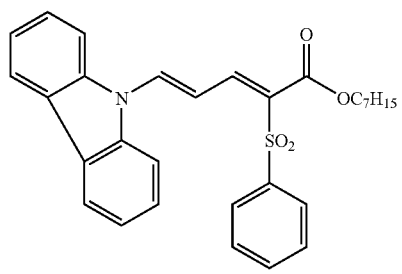
(I-18)
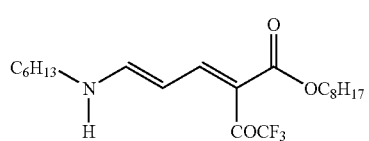
(I-19)
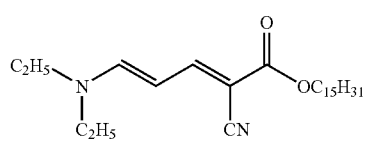
(I-20)
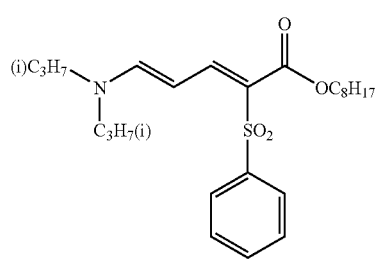
(II-1)
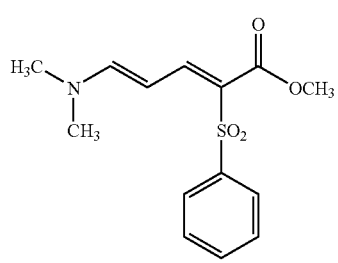
(II-2)
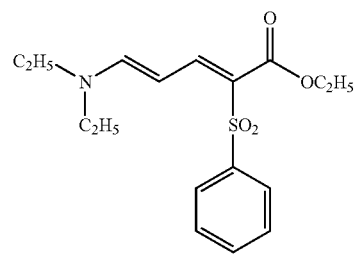
(II-3)
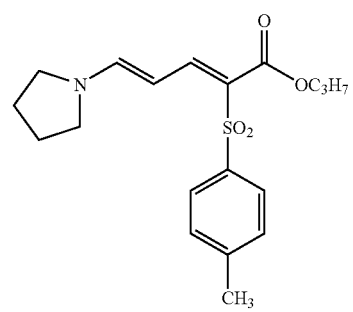
(II-4)
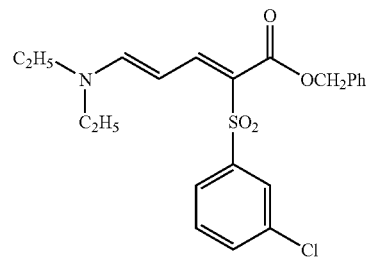
(II-5)
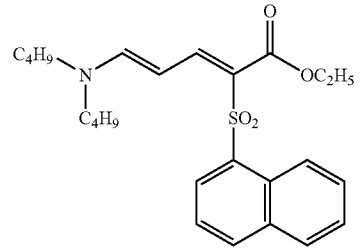
(II-6)
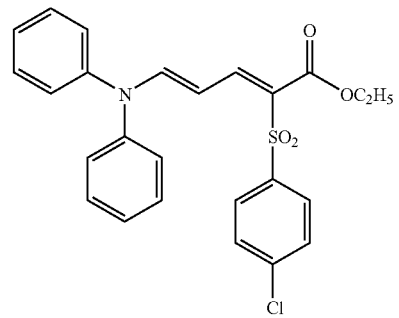
(II-7)
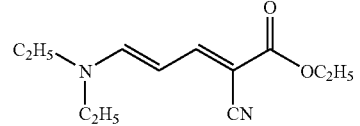

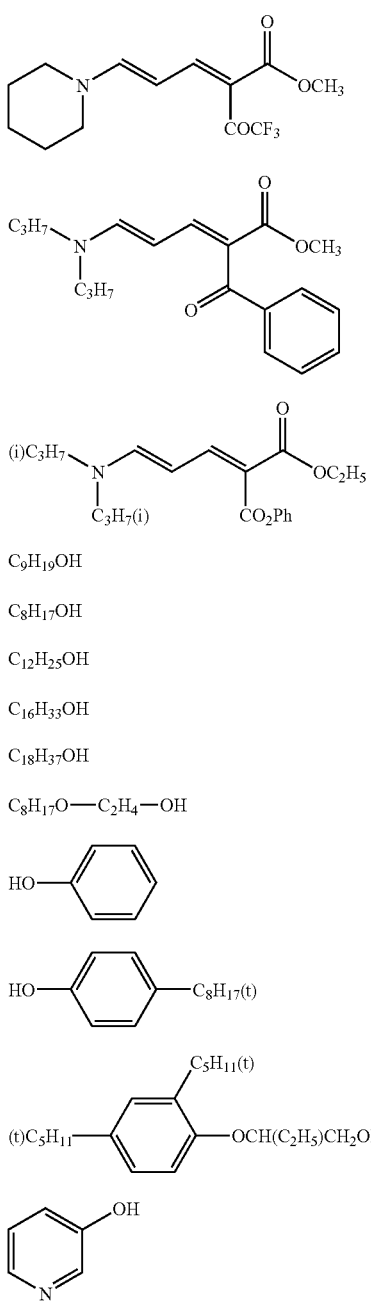

The reaction of a δ-aminopentadienoate derivative represented by formula (II) above with an alcohol represented by formula (III) above (hereinafter, referred to sometimes as "the reaction of an aspect of the invention") will be described.

The reaction of an aspect of the invention is an ester exchange reaction wherein a metal oxide or tetraalkyl titanate is preferably added as a catalyst and tetraalkyl titanate is more preferably added. Tetraalkyl titanate can be prepared from titanium tetrachloride and a compound represented by formula (IV), or commercially available tetraalkyl titanate may be obtained and used as it is.

$$R^{41}OH \quad (IV)$$

In formula (IV), $R^{41}$ represents an aliphatic group, an aromatic group, or a heterocyclic group bonded via a carbon atom.

When a compound represented by formula (IV) is used in excess amount and tetraalkyl titanate having a different alkyl group, for example, tetrabutyl titanate is added, tetraalkyl titanate having the alkyl in formula (IV) can be formed in an equilibrated state in the system to advance the reaction.

The alkyl in the tetraalkyl titanate added is preferably an alkyl having 1 to 20 carbon atoms, more preferably an alkyl having 2 to 10 carbon atoms. Specific examples of the tetraalkyl titanate include tetraisopropyl titanate, tetrapropyl titanate, tetrabutyl titanate and tetra(2-ethylhexyl)titanate, among which tetraisopropyl titanate and tetrabutyl titanate are preferable in respect of availability and reactivity, and tetrabutyl titanate is most preferable.

The amount of the tetraalkyl titanate added in the reaction of an aspect of the invention is 0.0001 to 0.9 mole, more preferably 0.001 to 0.7 mole, still more preferably 0.01 to 0.5 mole, further more preferably 0.05 to 0.2 mole, per 1 mole of the compound represented by formula (II).

The amount of the compound represented by formula (III) used in the reaction of an aspect of the invention is 0.8 to 100 moles, more preferably 0.9 to 20 moles, still more preferably 1.0 to 7 moles, further more preferably 1.5 to 5 moles, most preferably 2 to 4 moles, per 1 mole of the compound represented by formula (II).

The solvent used in the reaction of the invention includes, for example, amide-based solvents (for example, N,N-dimethylformamide, N,N-dimethylacetamide, and 1-methyl-2-pyrrolidone), sulfone-based solvents (for example, sulfolane), sulfoxide-based solvents (for example, dimethyl sulfoxide), ureido-based solvents (for example, tetramethyl urea), ether-based solvents (for example, dioxane and cyclopentyl methyl ether), hydrocarbon-based solvents (for example, toluene, xylene, and n-decane), halogen-based solvents (for example, tetrachloroethane and chlorobenzene), pyridine-based solvents (for example, pyridine, γ-picoline, and 2,6-lutidine) and nitrile-based solvents (for example, acetonitrile), and these are used alone or as a mixture thereof.

The solvent is preferably a sulfone-based solvent, a sulfoxide-based solvent, an ether-based solvent, a hydrocarbon-based solvent, a halogen-based solvent or a nitrile-based solvent, more preferably an ether-based solvent, a hydrocarbon-based solvent, a halogen-based solvent or a nitrile-based solvent, still more preferably an ether-based solvent, a hydrocarbon-based solvent or a halogen-based solvent. The reaction is carried out most preferably in the absence of a solvent.

The reaction temperature in the reaction of an aspect of the invention is preferably 0 to 250° C., more preferably 30 to 220° C., still more preferably 50 to 200° C., further more preferably 80 to 180° C.

In the reaction of an aspect of the invention, the residual alcohol represented by $R^{21}$—OH is preferably removed out of the reaction system, and therefore, the reaction is carried out preferably at normal pressures or under reduced pressure, more preferably under reduced pressure. Specifically, the reaction of an aspect of the invention is carried out preferably at 900 hPa or less, more preferably at 800 hPa or less, still more preferably 650 hPa or less. On the other hand, the reaction of an aspect of the invention is carried out preferably at 20 hPa or more.

The reaction time in the reaction of an aspect of the invention is 5 minutes to 20 hours, more preferably 30 minutes to 15 hours, still more preferably 1 to 10 hours. During the reaction, the temperature is preferably increased to 20 to 60° C. to complete the reaction.

The compound represented by formula (II), that is, the raw material in the reaction of an aspect of the invention, can be synthesized by referring to a method described in JP-A No. 2003-277349.

Hereinafter, exemplary embodiments of the present invention will be listed. However, the invention is not limited to the following exemplary embodiments.

[1]. A process for producing a δ-aminopentadienoate compound represented by the following formula (I), the process comprising reacting a δ-aminopentadienoate compound represented by the following formula (II) with an alcohol represented by the following formula (III):

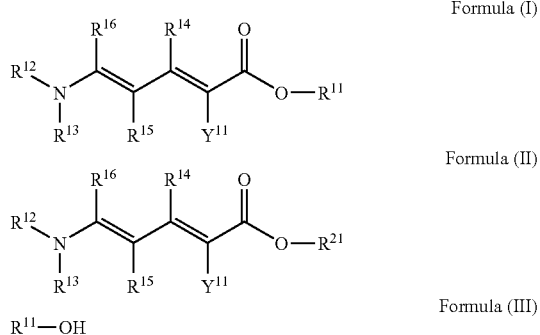

wherein in formulae (I) to (III), $R^{11}$ and $R^{21}$ each independently represent an aliphatic group, an aromatic group, or a heterocyclic group bonded via a carbon atom; $R^{12}$, $R^{13}$, $R^{14}$, $R^{15}$ and $R^{16}$ each independently represent a hydrogen atom, an aliphatic group, an aromatic group, or a heterocyclic group bonded via a carbon atom; $Y^{11}$ represents an electron-withdrawing group; $R^{12}$ and $R^{13}$ may be bonded to each other to form a ring; $R^{13}$ and $R^{15}$ may be bonded to each other to form a ring; $R^{15}$ and $Y^{11}$ may be bonded to each other to form a ring; $Y^{11}$ and $R^{11}$ may be bonded to each other to form a ring; $Y^{11}$ and $R^{21}$ may be bonded to each other to form a ring; $R^{11}$ and $R^{14}$ may be bonded to each other to form a ring; $R^{21}$ and $R^{14}$ may be bonded to each other to form a ring; $R^{14}$ and $R^{16}$ may be bonded to each other to form a ring; $R^{16}$ and $R^{12}$ may be bonded to each other to form a ring; and $R^{11}$ and $R^{21}$ are not the same group.

[2] The process for producing a δ-aminopentadienoate compound of [1], wherein tetraalkyl titanate is added as a catalyst in the reaction of the δ-aminopentadienoate compound represented by formula (II) with the alcohol represented by formula (III).

[3] The process for producing a δ-aminopentadienoate compound of [1], wherein $R^{21}$ in formula (II) is a methyl group or an ethyl group.

[4] The process for producing a δ-aminopentadienoate compound of [1], wherein the reaction of the δ-aminopentadienoate compound represented by formula (II) with the alcohol represented by formula (III) is carried out at 900 hPa or less.

[5] The process for producing a δ-aminopentadienoate compound of [1], wherein $R^{11}$ in formulae (I) and (III) is an alkyl group having 4 to 30 carbon atoms, an alkenyl group having 4 to 30 carbon atoms, an alkynyl group having 4 to 30 carbon atoms, an aralkyl group having 7 to 30 carbon atoms or an aryl group having 6 to 30 carbon atoms.

[6] The process for producing a δ-aminopentadienoate compound of [1], wherein $R^{11}$ in formulae (I) and (III) is an alkyl group having 6 to 20 carbon atoms or an alkenyl group having 6 to 20 carbon atoms.

[7] The process for producing a δ-aminopentadienoate compound of [1], wherein $R^{12}$ and $R^{13}$ in formulae (I) and (II) each independently represent a hydrogen atom, an alkyl group having 1 to 20 carbon atoms, an alkenyl group having 2 to 20 carbon atoms, an alkynyl group having 2 to 20 carbon atoms, or an aryl group having 6 to 20 carbon atoms.

[8] The process for producing a δ-aminopentadienoate compound of [1], wherein $R^{12}$ and $R^{13}$ in formulae (I) and (II) each independently represent an alkyl group having 1 to 8 carbon atoms or an aryl group having 6 to 8 carbon atoms.

[9] The process for producing a δ-aminopentadienoate compound of [1], wherein $R^{12}$ and $R^{13}$ in formulae (I) and (II) are the same.

[10] The process for producing a δ-aminopentadienoate compound of [1], wherein $R^{14}$, $R^{15}$ and $R^{16}$ in formulae (I) and (II) each independently represent a hydrogen atom, an alkyl group having 1 to 10 carbon atoms, or an aryl group having 6 to 10 carbon atoms.

[11] The process for producing a δ-aminopentadienoate compound of [1], wherein $R^{14}$, $R^{15}$ and $R^{16}$ in formulae (I) and (II) each independently represent a hydrogen atom or an alkyl group having 1 to 5 carbon atoms.

[12] The process for producing a δ-aminopentadienoate compound of [1], wherein $R^{21}$ in formula (II) is an alkyl group having 1 to 5 carbon atoms, an alkenyl group having 2 to 5 carbon atoms, or an alkynyl group having 2 to 5 carbon atoms.

[13] The process for producing a δ-aminopentadienoate compound of [1], wherein $Y^{11}$ in formulae (I) and (II) is an alkylsulfonyl group, an arylsulfonyl group, an acyl group, an arylcarbonyl group, a cyano group, an alkoxycarbonyl group, or an aryloxycarbonyl group.

[14] The process for producing a δ-aminopentadienoate compound of [1], wherein $Y^{11}$ in formulae (I) and (II) is an arenesulfonyl group having 6 to 15 carbon atoms.

EXAMPLES

Hereinafter, the present invention will be more specifically described referring to examples. However, the invention is not limited to these examples.

Example 1

Synthesis of Exemplary Compound (I-2)

Exemplary Compound (I-2) was synthesized according to the following scheme:

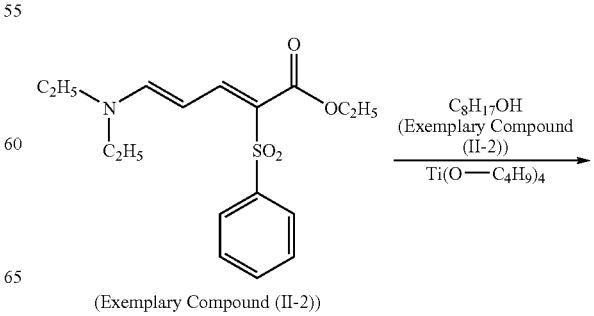

(Exemplary Compound (II-2))

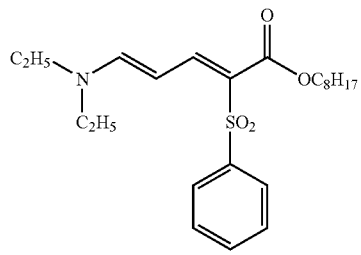

(Exemplary Compound (I-2))

100 g of Exemplary Compound (II-2) (synthesized according to Example 1 in JP-A No. 2003-277349; the yield was 82%; HPLC area ratio was 100%), 112 g of Exemplary Compound (III-2), and 10.0 g of tetrabutyl titanate were introduced into a three-neck flask and heated at an internal temperature of 150° C. for 6 hours under stirring, during which the flask was depressurized at 600 hPa to 28 hPa to remove 150 ml of distillate. Thereafter, the internal temperature was reduced to 20° C., then 2000 ml of n-hexane, 1000 ml of water and 200 ml of saturated saline were added for extraction, and the resulting organic layer was washed 3 times with a mixture of 1000 ml of water and 200 ml of saturated saline. The organic layer thus obtained was concentrated with a rotary evaporator, and the resulting residue was purified by silica gel column chromatography to give 123 g of objective Exemplary Compound (I-2) (yield 98%, HPLC area ratio 99.7%). Mass spectral measurement of this product indicated that M/E=421. NMR data on this product is as follows: NMR (CDCl$_3$): δ=7.993 (1H, d, J=12.8 Hz), 7.888 (2H, dd, J=1.6 Hz, 8.0 Hz), 7.3 to 7.5 (3H, m), 7.154 (1H, d, J=12.8 Hz), 6.537 (1H, t, J=12.8 Hz), 4.010 (2H, t, J=6.8 Hz), 3.3 to 3.4 (4H, m), 1.452 (2H, dd, J=7.2 Hz, 7.2 Hz), 1.0 to 1.4 Hz (16H, m), 0.897 (3H, t, J=7.0 Hz)

Example 2

Synthesis of Exemplary Compound (I-2)

Exemplary Compound (I-2) was synthesized according to the following scheme:

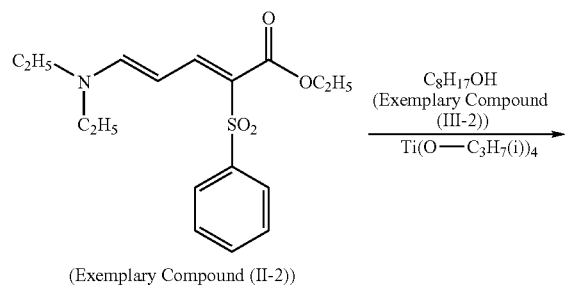

(Exemplary Compound (II-2))

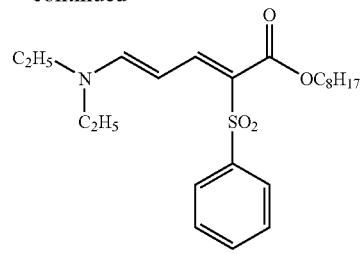

(Exemplary Compound (I-2))

100 g of Exemplary Compound (II-2) (synthesized according to Example 1 in JP-A No. 2003-277349; the yield was 82%; HPLC area ratio was 100%), 112 g of Exemplary Compound (III-2), and 8.4 g of tetraisopropyl titanate were introduced into a three-neck flask and heated at an internal temperature of 150° C. for 8 hours under stirring, during which the flask was depressurized at 550 hPa to 35 hPa to remove 140 ml of distillate. Thereafter, the internal temperature was reduced to 25° C., then 2000 ml of n-hexane, 1000 ml of water and 200 ml of saturated saline were added for extraction, and the resulting organic layer was washed 3 times with a mixture of 1000 ml of water and 200 ml of saturated saline. The organic layer thus obtained was concentrated with a rotary evaporator, and the resulting residue was purified by silica gel column chromatography to give 121 g of objective Exemplary Compound (I-2) (yield 97%, HPLC area ratio 99.7%). Mass spectral measurement of this product indicated that M/E=421.

Example 3

Synthesis of Exemplary Compound (I-1)

Exemplary Compound (I-1) was synthesized according to the following scheme:

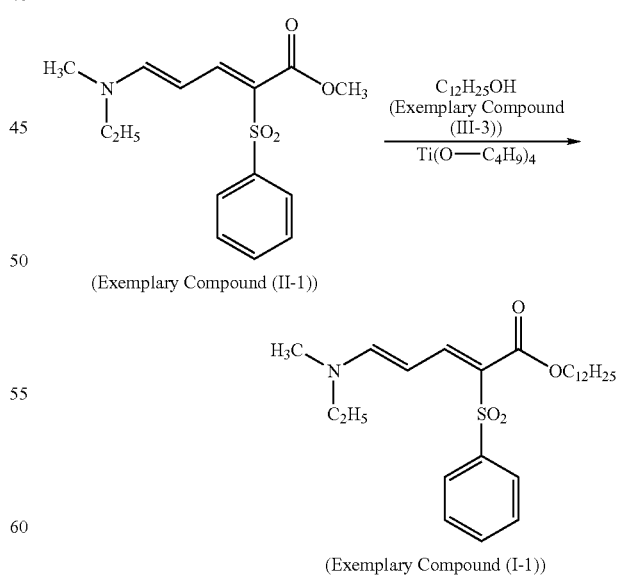

29.5 g of Exemplary Compound (II-1) (synthesized according to Example 1 in JP-A No. 2003-277349; the yield was 80%; HPLC area ratio was 99.7%), 54.0 g of Exemplary Compound (III-3), and 4.5 g of tetrabutyl titanate were introduced into a three-neck flask and heated at an internal temperature of 145° C. for 6 hours under stirring, during which the flask was depressurized at 600 hPa to 26 hPa to remove 150 ml of distillate. Thereafter, the internal temperature was reduced to 20° C., then 800 ml of n-hexane, 400 ml of water and 100 ml of saturated saline were added for extraction, and the resulting organic layer was washed 3 times with a mixture of 400 ml of water and 100 ml of saturated saline. The organic layer thus obtained was concentrated with a rotary evaporator, and the resulting residue was purified by silica gel column chromatography to give 44.1 g of objective Exemplary Compound (I-1) (yield 98%, HPLC area ratio 99.9%). Mass spectral measurement of this product indicated that M/E=449.

Example 4

Synthesis of Exemplary Compound (I-7)
Exemplary Compound (I-7) was synthesized according to the following scheme:

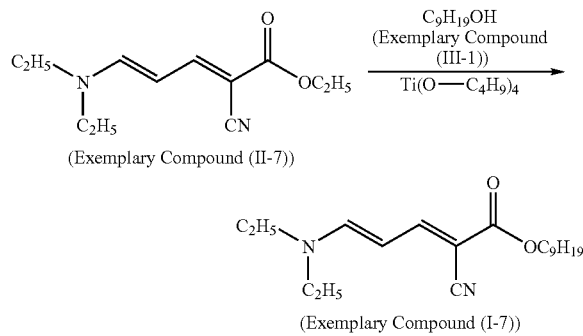

22.2 g of Exemplary Compound (II-7) (synthesized according to Example 1 in JP-A No. 2003-277349; the yield was 86%; HPLC area ratio was 99.8%), 43.3 g of Exemplary Compound (III-1), and 1.5 g of tetrabutyl titanate were introduced into a three-neck flask and heated at an internal temperature of 150° C. for 12 hours under stirring, during which the flask was depressurized at 600 hPa to 31 hPa to remove 140 ml of distillate. Thereafter, the internal temperature was reduced to 30° C., then 1000 ml of n-hexane, 500 ml of water and 100 ml of saturated saline were added for extraction, and the resulting organic layer was washed 3 times with a mixture of 500 ml of water and 100 ml of saturated saline. The organic layer thus obtained was concentrated with a rotary evaporator, and the resulting residue was purified by silica gel column chromatography to give 31.7 g of objective Exemplary Compound (I-7) (yield 99%, HPLC area ratio 99.9%). Mass spectral measurement of this product indicated that M/E=320.

Comparative Example 1

Exemplary Compound (I-2) was synthesized according to the following scheme (Synthesis (No. 1) according to JP-A No. 2003-277349):

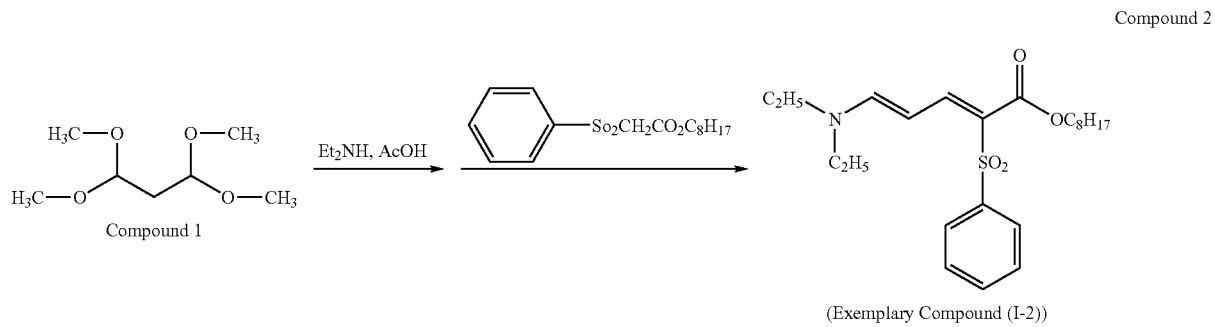

30.0 g of 1,3-bis-diethylaminotrimethinium diacetate (obtained by heating Compound 1, diethylamine and acetic acid, and then concentrating the mixture), 60 ml of N,N-dimethylacetamide, and 31.2 g of Compound 2 were mixed with one another, and 30.2 g of DBU (organic base: 1,8-diazabicyclo [5.4.0]undec-7-ene) was added dropwise, and the mixture was stirred at room temperature for 6 hours. Then, 500 ml of ethyl acetate, 400 ml of water and 100 ml of saturated saline were added for extraction, and the resulting ethyl acetate layer was washed 4 times with a mixture of 400 ml of water and 100 ml of saturated saline. The ethyl acetate layer thus obtained was concentrated with a rotary evaporator, and the resulting residue was purified by column chromatography to give 16.9 g of objective Exemplary Compound (I-2) (yield 40%, HPLC area ratio 99.6%). Mass spectral measurement of this product indicated that M/E=421.

Comparative Example 2

Exemplary Compound (I-2) was synthesized in the same manner as in Comparative Example 1 (Synthesis (No. 2) according to JP-A No. 2003-277349).

30.0 g of 1,3-bis-diethylaminotrimethinium diacetate (obtained by heating Compound 1, diethylamine and acetic acid, and then concentrating the mixture), 60 ml of N,N-dimethylacetamide, and 31.2 g of Compound 2 were mixed with one another, and 30.2 g of DBU (organic base: 1,8-diazabicyclo [5.4.0]undec-7-ene) was added dropwise, and the mixture was stirred at room temperature for 6 hours and then heated at 50° C. for additional 7 hours under stirring, and the disappearance of Compound 2 as the starting material in the reaction system was confirmed by TLC (thin layer chromatography). Then, 500 ml ethyl acetate, 400 ml of water and 100 ml of saturated saline were added for extraction, and the resulting ethyl acetate layer was washed 4 times with a mixture of 400 ml of water and 100 ml of saturated saline. The ethyl acetate layer thus obtained was concentrated with a rotary evaporator, and the resulting residue was purified by column chromatography to give 19.4 g of objective Exemplary Compound (I-2) (yield 46%, HPLC area ratio 99.6%). Mass spectral measurement of this product indicated that M/E=421.

Example 5

105.4 g of objective Exemplary Compound (I-2) was obtained (yield 84%, HPLC area ratio 99.6%) in the same manner as in Example 1 except that 14.3 g of zirconium acetylacetonate was used in place of 10.0 g of tetrabutyl titanate in Example 1.

Example 6

100 g of objective Exemplary Compound (I-2) was obtained (yield 80%, HPLC area ratio 99.6%) in the same manner as in Example 1 except that the reaction in the flask was carried out throughout at normal pressures instead of the reduced pressure of 600 to 28 hPa in Example 1.

As can be seen from the foregoing, a δ-aminopentadienoate derivative represented by formula (I) having a group (for example, a primary alkyl group having 8 to 20 carbon atoms) bonded to a desired carboxylic acid can be produced safely and economically in high yield in the Examples.

According to the invention, there can be provided a production process wherein a specific δ-aminopentadienoate derivative useful as an ultraviolet absorber for example is produced safely and economically in high yield by ester exchange.

All publications, patent applications, and technical standards mentioned in this specification are herein incorporated by reference to the same extent as if each individual publication, patent application, or technical standard was specifically and individually indicated to be incorporated by reference.

What is claimed is:

1. A process for producing a δ-aminopentadienoate compound represented by the following formula (I), the process comprising reacting a δ-aminopentadienoate compound represented by the following formula (II) with an alcohol represented by the following formula (III):

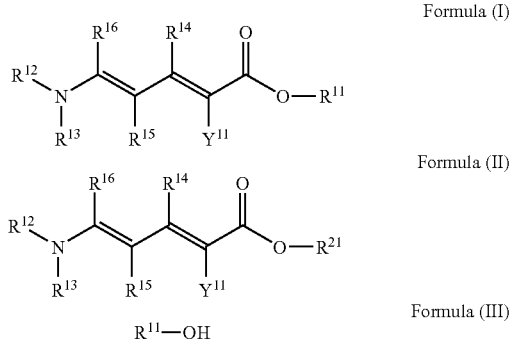

wherein in formulae (I) to (III), $R^{11}$ and $R^{21}$ each independently represent an aliphatic group, an aromatic group, or a heterocyclic group bonded via a carbon atom; $R^{12}$, $R^{13}$, $R^{14}$, $R^{15}$ and $R^{16}$ each independently represent a hydrogen atom, an aliphatic group, an aromatic group, or a heterocyclic group bonded via a carbon atom; $Y^{11}$ represents an electron-withdrawing group whose Hammett's substituent constant $\sigma_p$ value is a positive numerical value; $R^{12}$ and $R^{13}$ may be bonded to each other to form a ring; $R^{13}$ and $R^{15}$ may be bonded to each other to form a ring; $R^{15}$ and $Y^{11}$ may be bonded to each other to form a ring; $Y^{11}$ and $R^{11}$ may be bonded to each other to form a ring; $Y^{11}$ and $R^{21}$ may be bonded to each other to form a ring; $R^{11}$ and $R^{14}$ may be bonded to each other to form a ring; $R^{21}$ and $R^{14}$ may be bonded to each other to form a ring; $R^{14}$ and $R^{16}$ may be bonded to each other to form a ring; $R^{16}$ and $R^{12}$ may be bonded to each other to form a ring; and $R^{11}$ and $R^{21}$ are not the same group.

2. The process for producing a δ-aminopentadienoate compound of claim 1, wherein tetraalkyl titanate is added as a catalyst in the reaction of the δ-aminopentadienoate compound represented by formula (II) with the alcohol represented by formula (III).

3. The process for producing a δ-aminopentadienoate compound of claim 1, wherein $R^{21}$ in formula (II) is a methyl group or an ethyl group.

4. The process for producing a δ-aminopentadienoate compound of claim 1, wherein the reaction of the δ-aminopentadienoate compound represented by formula (II) with the alcohol represented by formula (III) is carried out at 900 hPa or less.

5. The process for producing a δ-aminopentadienoate compound of claim 1, wherein $R^{11}$ in formulae (I) and (III) is an alkyl group having 4 to 30 carbon atoms, an alkenyl group having 4 to 30 carbon atoms, an alkynyl group having 4 to 30 carbon atoms, an aralkyl group having 7 to 30 carbon atoms or an aryl group having 6 to 30 carbon atoms.

6. The process for producing a δ-aminopentadienoate compound of claim 1, wherein $R^{11}$ in formulae (I) and (III) is an alkyl group having 6 to 20 carbon atoms or an alkenyl group having 6 to 20 carbon atoms.

7. The process for producing a δ-aminopentadienoate compound of claim 1, wherein $R^{12}$ and $R^{13}$ in formulae (I) and (II) each independently represent a hydrogen atom, an alkyl group having 1 to 20 carbon atoms, an alkenyl group having 2 to 20 carbon atoms, an alkynyl group having 2 to 20 carbon atoms, or an aryl group having 6 to 20 carbon atoms.

8. The process for producing a δ-aminopentadienoate compound of claim 1, wherein $R^{12}$ and $R^{13}$ in formulae (I) and (II) each independently represent an alkyl group having 1 to 8 carbon atoms or an aryl group having 6 to 8 carbon atoms.

9. The process for producing a δ-aminopentadienoate compound of claim 1, wherein $R^{12}$ and $R^{13}$ in formulae (I) and (II) are the same.

10. The process for producing a δ-aminopentadienoate compound of claim 1, wherein $R^{14}$, $R^{15}$ and $R^{16}$ in formulae (I) and (II) each independently represent a hydrogen atom, an alkyl group having 1 to 10 carbon atoms, or an aryl group having 6 to 10 carbon atoms.

11. The process for producing a δ-aminopentadienoate compound of claim 1, wherein $R^{14}$, $R^{15}$ and $R^{16}$ in formulae (I) and (II) each independently represent a hydrogen atom or an alkyl group having 1 to 5 carbon atoms.

12. The process for producing a δ-aminopentadienoate compound of claim 1, wherein $R^{21}$ in formula (II) is an alkyl group having 1 to 5 carbon atoms, an alkenyl group having 2 to 5 carbon atoms, or an alkynyl group having 2 to 5 carbon atoms.

13. The process for producing a δ-aminopentadienoate compound of claim 1, wherein $Y^{11}$ in formulae (I) and (II) is an alkylsulfonyl group, an arylsulfonyl group, an acyl group, an arylcarbonyl group, a cyano group, an alkoxycarbonyl group, or an aryloxycarbonyl group.

14. The process for producing a δ-aminopentadienoate compound of claim 1, wherein $Y^{11}$ in formulae (I) and (II) is an arenesulfonyl group having 6 to 15 carbon atoms.

15. The process for producing a δ-aminopentadienoate compound of claim 1, wherein in formulae (I) and (II), $Y^{11}$ represents a phenylsulfonyl, carbonyl or cyano group, $R^{14}$-

$R^{16}$ represent hydrogen atoms, $R^{12}$ and $R^{13}$ represent a simple straight chain alkyl, form a simple heterocycle, or represent a phenyl.

16. The process for producing a δ-aminopentadienoate compound of claim 1, wherein $R^{11}$ in formulae (I) and (III) represents a primary alkyl group having 8 to 20 carbon atoms, $R^{12}$ and $R^{13}$ in formulae (I) and (II) represent a primary alkyl group having 1 to 5 carbon atoms, $R^{14}$, $R^{15}$ and $R^{16}$ in formulae (I) and (II) represent hydrogen atoms, $R^{21}$ in formula (II) represents an alkyl group having 1 to 4 carbon atoms, and $Y^{11}$ in formulae (I) and (II) represents a benzenesulfonyl group.

* * * * *